Nov. 19, 1940. O. KAUSEN Plant Pat. 432
RHODODENDRON PLANT
Filed Sept. 6, 1939
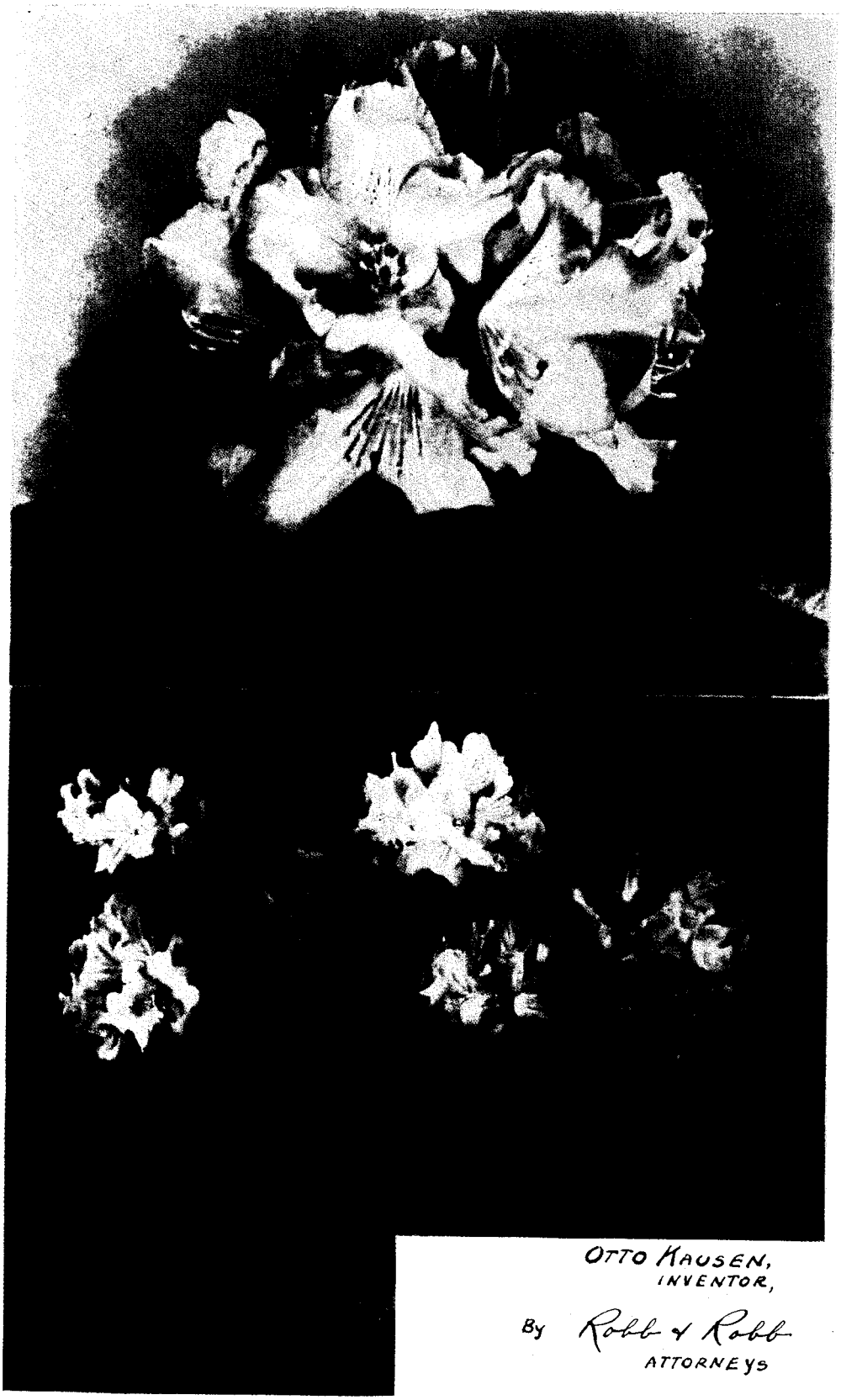
OTTO KAUSEN,
INVENTOR,
By Robb & Robb
ATTORNEYS Patented Nov. 19, 1940

Plant Pat. 432

UNITED STATES PATENT OFFICE

432

RHODODENDRON PLANT

Otto Kausen, Eureka, Calif., assignor to Cottage Gardens Company Inc., Eureka, Calif.

Application September 6, 1939, Serial No. 293,629

1 Claim. (Cl. 47—60)

This invention relates to a new and distinct variety of rhododendron characterized particularly by the large size and distinctive coloring of its flowers, the time of blooming of the plant and the habit of growth of the latter.

My new variety of rhododendron is a true hybrid seedling resulting from the crossing of two distinct and different varieties of rhododendron, namely, rhododendron Blush Pearl and rhododendron Blandyanum, being respectively the seed parent and the pollen parent of my new variety in the hybridization thereof.

The color of the flowers of my new variety of rhododendron is distinctively different from that of either of its parent varieties. A flower of rhododendron Blush Pearl is generally white, though the white is tinged with pink upon opening. Rhododendron Blandyanum has flowers of generally rosy crimson. The flowers of my new variety combine rich hues of reds and pinks, intermediate the pink of Blush Pearl and the crimson of Blandyanum.

My new variety of rhododendron is generally compact in habit of growth, though taller and less compact than its parent Blandyanum which is a low and very compact grower. While my new variety has a tendency toward the tallness of growth of its parent Blush Pearl, it is much more compact than the latter which is rather loose in manner of growth. My new variety is slower in habit of growth than its parent Blush Pearl, and a somewhat more rapid grower than its parent Blandyanum.

Both my new variety and its parent Blush Pearl have large flowers and large flower trusses. The flower trusses of Blush Pearl are very loose, while those of my new variety are very compact.

The flower buds of both my new variety and its parent Blush Pearl are very large, but the former are quite round whereas the latter are long and slender. The flower buds of Blandyanum are very small, round and short and the flowers of the latter are of medium size.

The leaves of my new variety differ considerably from the leaves of either of its parent varieties. The leaves of rhododendron Blush Pearl are very long and straight and the surfaces thereof are inclined to be ridged and rough. The leaves of rhododendron Blandyanum are long, narrow and pointed, the upper surface being smooth and the under surface being coated with a fuzzy tissue. My new variety has leaves which are wider and shorter than Blush Pearl, with a more rounded leaf point than the latter and the surfaces of the leaves of my new variety are very smooth and lack the characteristic fuzzy coating of the under surface of Blandyanum leaves. The coloring of the leaves of my new variety is much lighter green than that of its parent Blush Pearl.

My new variety of rhododendron first puts forth buds during the month of July when grown out of doors in the vicinity of Eureka, California. The July flower buds remain dormant on the plants until the following spring. Plants of my new variety grown out of doors in the vicinity of Eureka, California, ordinarily bloom during the month of April, depending of course upon weather conditions, and the length of the flowering period is generally about three weeks. My new variety and its parent Blush Pearl are both classed as early blooming rhododendrons. My new variety, however, begins to bloom slightly later than Blush Pearl so that time of blooming of my new variety is intermediate that of its parents since Blandyanum begins to bloom in midseason, somewhat later than my new variety.

My new variety of rhododendron has been asexually reproduced, propagation being accomplished by means of cuttings, and plants of my variety so reproduced have been found to retain their distinguishing characteristics and the same are believed to be fixed and permanent.

The following is a detailed description of my new variety of rhododendron:

*Flower*

(Observations made in reference to plants grown out of doors in the vicinity of Eureka, California.)

When plant first puts forth buds: During the month of July.

Time of flowering: During the month of April, subject to weather conditions. Early blooming variety.

Length of flowering period: A plant of the new variety will flower over a period of approximately three weeks measured from the time the first bud has opened until all buds have opened and flowered.

Keeping qualities of individual blooms: Individual blooms last about ten days, depending upon weather conditions.

Number of blooms to a stem: One to three—in clusters.

Size of blooms: The blooms are made up of a number of individual flowers, the individual flowers being somewhat bell-shaped and measuring approximately three inches in diameter when fully opened. The individual flowers are single, and their outer edges are scalloped.

Average number of blooms to a plant: An average plant of 12 inches to 18 inches (diameter of crown) grade will produce ten flowers per season.

Bud: Large and round. Dimensions of dormant flower bud: approximately two and one-fourth inches in circumference; approximately one and one-fourth inches from base to tip of flower bud.

*Genital organs*

Stamens, anthers are medium size. Anthers are reddish brown. They are regular around styles.

Stamens—Filaments: Filaments are long.

Color.—Delicate pink.

Pollen: White.

Styles: Loosely separated.

Stigmas: Brown.

Ovaries: Protruding from calyx.

Color: (Compared with "Color Standards and Color Nomenclature" by Ridgeway—description made from plants grown out of doors at Eureka, California. Plants fully open.)

The veins or thicker portions of the flower on the underneath or back side from the base to the tips is Rose color as color patch Plate XII, color or line No. 71, tone *b*.

The back of the flower in between these portions is Deep Rose Pink XII—71—*d*.

The top or upper side of the flower is graduated from Tyrian Pink XII—69—*b* at the tips to White LIII—67''''' V—R at the base.

Stamens are rather long and the tips are Tyrian Pink XII—69—*b* and graduating to White LIII—67''''' V—R at the base.

On the top of the inside of the flower there is one patch of spots approximately ⅔ of the way out from the base. They vary in size from a pin point and are irregular up to ¼'' long. Their color is best described as being Vandyke Red, Plate XIII—1'—K.

*Plant*

General shape of plant: Medium tall and medium compact.

Foliage: Smooth, oblong, heavy leaves; medium green color. Dimensions of leaves: approximately six inches long and two and three-fourths inches in diameter.

Flower trusses: Large and compact; approximately sixteen inches in circumference and seven inches tall from base to highest point of flower (when fully opened.)

Rapidity of growth: Medium.

Having thus described my invention, what I claim is new and desire to secure by Plant Letters Patent of the United States is:

A new and distinct variety of rhododendron plant substantially as shown and described, characterized by the distinctive color of its flower, blooming habit and manner of growth.

OTTO KAUSEN.